United States Patent
Takeuchi et al.

(10) Patent No.: US 10,039,303 B2
(45) Date of Patent: Aug. 7, 2018

(54) CHLOROGENIC ACID-CONTAINING COMPOSITION, METHOD FOR MANUFACTURING SAME, AND DRINK OR FOOD ITEM

(71) Applicant: FUJIFILM CORPORATION, Minato-ku, Tokyo (JP)

(72) Inventors: Kiyoshi Takeuchi, Kanagawa (JP); Yasuhiro Aiki, Kanagawa (JP); Kozo Sato, Kanagawa (JP); Fumio Mogi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/081,940

(22) Filed: Mar. 28, 2016

(65) Prior Publication Data

US 2016/0213042 A1    Jul. 28, 2016

Related U.S. Application Data

(63) Continuation of application No. PCT/JP2014/075283, filed on Sep. 24, 2014.

(30) Foreign Application Priority Data

Oct. 4, 2013   (JP) .................................. 2013-209537
Feb. 10, 2014  (JP) .................................. 2014-023856

(51) Int. Cl.
| | | |
|---|---|---|
| *A61K 36/28* | (2006.01) | |
| *A23L 1/30* | (2006.01) | |
| *C09K 15/08* | (2006.01) | |
| *C07C 67/48* | (2006.01) | |
| *C07C 67/56* | (2006.01) | |
| *A61K 31/216* | (2006.01) | |
| *C12P 7/06* | (2006.01) | |
| *A23L 33/105* | (2016.01) | |
| *A23L 33/20* | (2016.01) | |

(52) U.S. Cl.
CPC ........... *A23L 1/3002* (2013.01); *A23L 33/105* (2016.08); *A23L 33/20* (2016.08); *A61K 31/216* (2013.01); *A61K 36/28* (2013.01); *C07C 67/48* (2013.01); *C07C 67/56* (2013.01); *C09K 15/08* (2013.01); *C12P 7/06* (2013.01); *A23V 2002/00* (2013.01); *Y02E 50/17* (2013.01)

(58) Field of Classification Search
CPC ...................................................... A61K 36/28
USPC ....................................................... 424/764
See application file for complete search history.

(56) References Cited

U.S. PATENT DOCUMENTS

| | | | |
|---|---|---|---|
| 4,072,671 A | | 2/1978 | Sodini |
| 4,551,335 A | * | 11/1985 | Canella .................. A23L 11/37 426/44 |
| 2014/0135391 A1 | | 5/2014 | Yamawaki et al. |

FOREIGN PATENT DOCUMENTS

| | | |
|---|---|---|
| CN | 1531863 A | 9/2004 |
| CN | 1740137 A | 3/2006 |
| CN | 1762972 A | 4/2006 |
| JP | H09-143465 A | 6/1997 |
| JP | 2000-063827 | 2/2000 |
| JP | 2000063827 A * | 2/2000 |
| WO | 2012/176845 A1 | 12/2012 |
| WO | 2014/060244 A1 | 4/2014 |

OTHER PUBLICATIONS

International Search Report issued in International Application No. PCT/JP2014/075283 dated Jan. 6, 2015.
Written Opinion of the ISA issued in International Application No. PCT/JP2014/075283 dated Jan. 6, 2015.
Japanese Office Action dated Nov. 22, 2016 in corresponding Japanese Patent Application No. 2014-23856 and a Partial English Translation thereof.
English language translation of the following: Office action dated Dec. 27, 2016 from the SIPO in a Chinese patent application No. 201400536641.1 corresponding to the instant patent application. This office action translation is submitted now in order to supplement the understanding of the cited reference which is being disclosed in the instant Information Disclosure Statement.
Extended European Search Report dated Aug. 31, 2016, issued in corresponding EP Patent Application.
English language translation of the following: Office action dated May 25, 2017 from the SIPO in a Chinese patent application No. 201480053641.1 corresponding to the instant patent application. This office action translation is submitted now in order to supplement the understanding of the cited reference which is being disclosed in the instant Information Disclosure Statement.

* cited by examiner

*Primary Examiner* — Christopher Robin Tate
*Assistant Examiner* — Deborah A Davis
(74) *Attorney, Agent, or Firm* — Solaris Intellectual Property Group, PLLC

(57) ABSTRACT

Provided are a method for manufacturing a chlorogenic acid-containing composition, including a chlorogenic acid extraction step of obtaining a chlorogenic acid-containing liquid extract from sunflower seed residues remaining after oil expression by bringing chlorogenic acid and saccharides derived from the sunflower seed residues remaining after oil expression into contact with yeast and a solvent selected from the group consisting of water, an alcohol, and a liquid mixture of water and an alcohol, and a bacterial treatment step of performing at least one treatment selected from germicidal treatment or sterilization treatment on the liquid extract, a chlorogenic acid-containing composition obtained by the manufacturing method, and a drink or food item containing the chlorogenic acid-containing composition.

9 Claims, No Drawings

CHLOROGENIC ACID-CONTAINING COMPOSITION, METHOD FOR MANUFACTURING SAME, AND DRINK OR FOOD ITEM

CROSS-REFERENCE TO RELATED APPLICATIONS

This application is a continuation application of International Application No. PCT/JP2014/075283, filed Sep. 24, 2014, the disclosure of which is incorporated herein by reference in its entirety. Further, this application claims priority from Japanese Patent Application No. 2013-209537, filed Oct. 4, 2013, and Japanese Patent Application No. 2014-023856, filed Feb. 10, 2014, the disclosures of which are incorporated herein by reference in their entireties.

BACKGROUND OF THE INVENTION

1. Field of the Invention

The present invention relates to a chlorogenic acid-containing composition, a method for manufacturing the same, and a drink or food item.

2. Description of the Related Art

Sunflower seeds or a residue thereof remaining after oil expression are known to contain chlorogenic acid. Due to its diverse physiological activities such as antioxidative activity, blood pressure improving activity, and inhibitory activity against rise in blood glucose level, chlorogenic acid has been expected to become a raw material for pharmaceutical products, cosmetics, health foods, food additives, and the like in recent years.

As methods for obtaining a chlorogenic acid-containing extract from sunflower seeds or residues thereof remaining after oil expression, for instance, a method (for example, see JP2000-063827A) for obtaining a chlorogenic acid-containing liquid extract by hot water extraction, hydroalcohol extraction, or the like and then making the liquid extract into powder or paste by vacuum concentration, a method (for example, see CN1740137A) for obtaining a chlorogenic acid-containing liquid extract by alcohol extraction and then bringing the liquid extract into contact with an adsorbent resin, and the like are known.

SUMMARY OF THE INVENTION

However, in the method described in JP2000-063827A, saccharides such as sucrose or raffinose are also extracted together with chlorogenic acid, and hence the calories in the extract increase. Particularly, by the extraction of chlorogenic acid from sunflower seeds, a large amount of lipids are extracted as well, and hence the calories in the extract increase further. Because a chlorogenic acid-containing extract containing a large amount of high-calorie saccharides and lipids may lead to hyperglycemia, obesity, and the like, it is not preferable to use the extract in health foods, food additives, and the like.

Although the method described in CN1740137A makes it possible to obtain an extract containing high-purity chlorogenic acid, the method has problems such as complicated operations, high costs, and the like.

Therefore, there is a demand for a method making it possible to obtain a chlorogenic acid-containing composition with calories lower than calories of a chlorogenic acid-containing composition, which is obtained by the method of the related art using sunflower seeds or residues thereof remaining after oil expression as a raw material, by a simple operation.

The present invention has been made under the circumstances described above, and objects thereof are to provide a method for manufacturing a chlorogenic acid-containing composition making it possible to obtain a chlorogenic acid-containing composition with calories lower than calories of a chlorogenic acid-containing composition, which is obtained by the method of the related art using sunflower seed residues remaining after oil expression as a raw material, by a simple operation, to provide a chlorogenic acid-containing composition obtained by the manufacturing method, and to provide a drink or food item containing the chlorogenic acid-containing composition.

Specific means for achieving the above objects are as below.

<1> A method for manufacturing a chlorogenic acid-containing composition, including a chlorogenic acid extraction step of obtaining a chlorogenic acid-containing liquid extract from sunflower seed residues remaining after oil expression by bringing chlorogenic acid and saccharides derived from the sunflower seed residues remaining after oil expression into contact with yeast and a solvent selected from the group consisting of water, an alcohol, and a liquid mixture of water and alcohol, and a bacterial treatment step of performing at least one treatment selected from germicidal treatment or sterilization treatment on the liquid extract.

<2> The method for manufacturing a chlorogenic acid-containing composition described in <1>, in which the chlorogenic acid extraction step includes a step of obtaining a liquid extract by bringing the sunflower seed residues remaining after oil expression into contact with a solvent, and a step of obtaining a chlorogenic acid-containing liquid extract by bringing the obtained liquid extract into contact with yeast.

<3> The method for manufacturing a chlorogenic acid-containing composition described in <1>, in which the chlorogenic acid extraction step includes a step of obtaining a mixture by mixing the sunflower seed residues remaining after oil expression with the yeast and a step of obtaining a chlorogenic acid-containing liquid extract by bringing the obtained mixture into contact with the solvent.

<4> The method for manufacturing a chlorogenic acid-containing composition described in <1>, in which the chlorogenic acid extraction step includes a step of obtaining a chlorogenic acid-containing liquid extract by bringing the sunflower seed residues remaining after oil expression into contact with the solvent in the presence of yeast.

<5> The method for manufacturing a chlorogenic acid-containing composition described in any one of <1> to <4>, in which the yeast is baker's yeast.

<6> The method for manufacturing a chlorogenic acid-containing composition described in any one of <1> to <5>, in which the solvent is water.

<7> The method for manufacturing a chlorogenic acid-containing composition described in any one of <1> to <6>, in which the chlorogenic acid and the saccharides derived from the sunflower seed residues remaining after oil expression are brought into contact with the yeast under a temperature condition of 20° C. to 50° C.

<8> The method for manufacturing a chlorogenic acid-containing composition described in any one of <1> to <7>, further including a step of obtaining chlorogenic acid-containing composition powder by drying the chlorogenic acid-containing liquid extract, after the bacterial treatment step.

<9> A chlorogenic acid-containing composition obtained by the manufacturing method described in any one of <1> to <8>.

<10> A drink or food item containing the chlorogenic acid-containing composition described in <9>.

In the present specification, a range of numerical values represented using "to" means a range including numerical values listed before and after "to" as a lower limit and an upper limit respectively.

In the present specification, in a case where the amount of each of the components in a composition is mentioned, if there is a plurality of substances corresponding to each of the components in the composition, unless otherwise specified, the amount of each of the components means a total amount of the plurality of substances present in the composition.

In the present specification, a term "step" includes not only an independent step but also a step which cannot be clearly distinguished from other steps as long as the intended object of the step is achieved.

According to the present invention, it is possible to provide a method for manufacturing a chlorogenic acid-containing composition making it possible to obtain a chlorogenic acid-containing composition with calories lower than calories of a chlorogenic acid-containing composition, which is obtained by the method of the related art using sunflower seed residues remaining after oil expression as a raw material, by a simple operation, to provide a chlorogenic acid-containing composition obtained by the manufacturing method, and to provide a drink or food item containing the chlorogenic acid-containing composition.

DESCRIPTION OF THE PREFERRED EMBODIMENTS

Hereinafter, specific embodiments of the present invention will be described in detail, but the present invention is not limited to the following embodiment. Within an intended scope of the present invention, the present invention can be embodied by adding modification as appropriate.

[Method for Manufacturing Chlorogenic Acid-Containing Composition]

The method for manufacturing a chlorogenic acid-containing composition of the present invention is a method for manufacturing a chlorogenic acid-containing composition, including a chlorogenic acid extraction step of obtaining a chlorogenic acid-containing liquid extract from sunflower seed residues remaining after oil expression by bringing chlorogenic acid and saccharides derived from the sunflower seed residues remaining after oil expression into contact with yeast and a solvent selected from the group consisting of water, an alcohol, and a liquid mixture of water and an alcohol, and a bacterial treatment step of performing at least one treatment selected from germicidal treatment or sterilization treatment on the liquid extract.

According to the manufacturing method of the present invention, it is possible to obtain a chlorogenic acid-containing composition with calories lower than calories of a chlorogenic acid-containing composition, which is obtained by the method of the related art using sunflower seed residues remaining after oil expression as a raw material, by a simple operation.

The operation mechanism of the present invention is unclear but is presumed to be as below by the inventors of the present invention.

The sunflower seed residues remaining after oil expression contain disaccharides such as sucrose and trisaccharides such as raffinose in addition to the chlorogenic acid. If the sunflower seed residues remaining after oil expression are brought into contact with a solvent so as to extract the chlorogenic acid, the disaccharides and trisaccharides are extracted together with the chlorogenic acid. Consequently, simply with the method of the related art that is for obtaining a solvent extract from the sunflower seed residues remaining after oil expression, a chlorogenic acid-containing extract containing sucrose, raffinose, and the like with relatively high calories is obtained. Although there is also a method for removing the disaccharides and trisaccharides by performing purification treatment such as bringing the obtained chlorogenic acid-containing liquid extract into contact with an adsorbent resin, the operation of the method tends to be complicated, and the costs thereof tend to be high.

In the method for manufacturing a chlorogenic acid-containing composition of the present invention, by bringing the chlorogenic acid and saccharides derived from the sunflower seed residues remaining after oil expression, that is, the chlorogenic acid and saccharides contained in the sunflower seed residues remaining after oil expression into contact with yeast and a solvent selected from the group consisting of water, an alcohol, and a liquid mixture of water and an alcohol, the saccharides contained in the sunflower seed residues remaining after oil expression are decomposed by alcohol fermentation caused by the yeast, and the chlorogenic acid contained in the sunflower seed residues remaining after oil expression is extracted.

The saccharides such as sucrose and raffinose contained in the sunflower seed residues remaining after oil expression are saccharides that can be a substrate of a fermentation reaction caused by yeast. Through the alcohol fermentation caused by yeast, the saccharides are decomposed into ethanol, carbon dioxide, and the like. For example, by coming into contact with yeast, sucrose is hydrolyzed into glucose and fructose and finally decomposed into ethanol and carbon dioxide. Furthermore, by coming into contact with yeast, raffinose is hydrolyzed into melibiose and fructose, and fructose is finally decomposed into ethanol and carbon dioxide. Although melibiose tends to remain as it is, it is not easily absorbed and digested because of being an indigestible sugar, and accordingly, the calories thereof are lower than that of other saccharides in the same amount. In contrast, the chlorogenic acid is not decomposed by yeast.

It is considered that for this reason, the liquid extract, which is obtained by bringing the chlorogenic acid and saccharides derived from the sunflower seed residues remaining after oil expression into contact with yeast and a solvent selected from the group consisting of water, an alcohol, and liquid mixture of water and an alcohol, becomes a chlorogenic acid-containing liquid extract in which the calories resulting from the saccharides are reduced.

In the method for manufacturing a chlorogenic acid-containing composition of the present invention, at least one treatment selected from germicidal treatment or sterilization treatment is performed on the liquid extract obtained by bringing the chlorogenic acid and saccharides derived from the sunflower seed residues remaining after oil expression into contact with yeast and a solvent selected from the group consisting of water, an alcohol, and liquid mixture of water and an alcohol. If viable cells of yeast or other bacteria (for example, spoilage bacteria contained in the sunflower seed residues remaining after oil expression, airborne bacteria, and the like) are present in the liquid extract, the chlorogenic acid may be decomposed or altered, and this may lead to deterioration of stability of the chlorogenic acid-containing composition. According to the method for manufacturing a chlorogenic acid-containing composition of the present invention, at least one treatment selected from germicidal treatment or sterilization treatment is performed on the liquid extract obtained as above. Therefore, the finally obtained chlorogenic acid-containing composition is excellent in quality stability and preservation stability.

Hereinafter, the chlorogenic acid in the present invention will be described, and then each of the steps included in the method for manufacturing a chlorogenic acid-containing composition of the present invention will be specifically described.

In the present invention, the "chlorogenic acid" means all of the chlorogenic acid, chlorogenic acid isomers, and chlorogenic acid derivatives (hereinafter, referred to as "chlorogenic acids" as appropriate).

The "chlorogenic acids" is a generic name of a group of compounds represented by the following Formula (1). In these compounds, 1 to 3 out of 4 hydroxyl groups of quinic acid represented by Formula (1-1) form an ester bond with a partial structure of caffeic acid represented by Formula (1-2), and the quinic acid portion represented by Formula (1-1) has a carboxyl group.

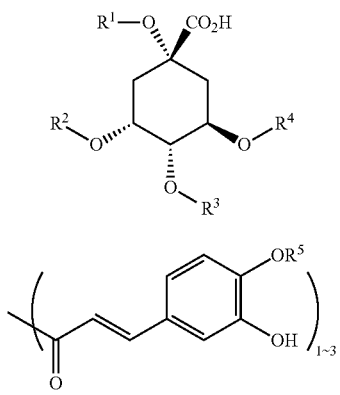

In Formula (1), each of $R^1$, $R^2$, $R^3$, and $R^4$ independently represents a hydrogen atom or a partial structure represented by Formula (1-2). One to three out of $R^1$, $R^2$, $R^3$, and $R^4$ are the partial structure represented by Formula (1-2). $R^5$ represents a hydrogen atom or a methyl group.

Examples of the chlorogenic acid derivatives include a compound in which $R^5$ in the partial structure represented by Formula (1) is other than a hydrogen atom and represents, for example, an alkyl group such as a methyl group. Such a chlorogenic acid derivative can also be contained in the chlorogenic acid-containing composition obtained by the manufacturing method of the present invention.

The main component of the chlorogenic acid contained in the sunflower seed residues remaining after oil expression is a compound represented by Formula (1) in which each of $R^1$, $R^2$, $R^3$, and $R^5$ represents a hydrogen atom and $R^4$ is a partial structure of caffeic acid represented by Formula (1-2). Herein, the "main component" means a component whose content is equal to or greater than 50% by mass.

<Chlorogenic Acid Extraction Step>

The method for manufacturing a chlorogenic acid-containing composition of the present invention includes a chlorogenic acid extraction step of obtaining a chlorogenic acid-containing liquid extract from sunflower seed residues remaining after oil expression by bringing the chlorogenic acid and saccharides derived from the sunflower seed residues remaining after oil expression into contact with yeast and a solvent selected from the group consisting of water, an alcohol, and a liquid mixture of water and an alcohol.

According to the chlorogenic acid extraction step, it is possible to obtain a liquid extract containing chlorogenic acid contained in the sunflower seed residues remaining after oil expression. Furthermore, according to the chlorogenic acid extraction step, disaccharides such as sucrose, trisaccharides such as raffinose, and the like contained in the sunflower seed residues remaining after oil expression are decomposed by alcohol fermentation caused by yeast. Therefore, the obtained liquid extract becomes a chlorogenic acid-containing liquid extract in which the calories resulting from the sucrose, the raffinose, and the like are reduced.

In the method for manufacturing a chlorogenic acid-containing composition of the present invention, sunflower seed residues remaining after oil expression are used as a raw material. In the present invention, the "sunflower seed" refers to a seed called achene of a sunflower (scientific name: Helianthus annuus L.) of genus Helianthus in Asteraceae family. The sunflower seed contains a large amount of chlorogenic acid and a large amount of lipid. Therefore, if the sunflower seed is directly used as a raw material, due to the calories resulting from the lipid, the calories of the chlorogenic acid-containing composition also increase. In the present invention, by using the sunflower seed residues remaining after oil expression as a raw material, the calories resulting from the lipid of the chlorogenic acid-containing composition are reduced.

In the present invention, the "saccharides derived from sunflower seed residues remaining after oil expression" mean saccharides contained in the sunflower seed residues remaining after oil expression. The saccharids derived from the sunflower seed residues remaining after oil expression are not particularly limited as long as they are fermented by yeast. Examples of the saccharides derived from the sunflower seed residues remaining after oil expression include monosaccharides such as glucose and fructose, disaccharides such as sucrose, trisaccharides such as raffinose, and the like.

The yeast in the present invention is not particularly limited. Examples of the yeast in the present invention include baker's yeast, beer yeast, wine yeast, sake yeast, and the like. Among these, as the yeast in the present invention, yeast that belongs to the species Saccharomyces cerevisiae is preferable because the yeast can efficiently decompose the saccharides contained in the sunflower seed residues remaining after oil expression. One kind of the yeast may be used singly, or two or more kinds thereof may be used concurrently. From the viewpoint of availability and price, the yeast in the present invention is preferably at least one kind of yeast selected from the group consisting of baker's yeast and beer yeast, and more preferably baker's yeast. The manufacturing company of the baker's yeast is not particularly limited, but is preferably Oriental Yeast Co., ltd. or Lesaffre (France).

The yeast in the present invention may be live yeast, dry yeast, or semi-dry yeast.

In the present invention, the solvent coming into contact with the chlorogenic acid and saccharides derived from the sunflower seed residues remaining after oil expression and with yeast, that is, the extraction solvent is a solvent selected from the group consisting of water, an alcohol, and a liquid mixture of water and an alcohol. Among these, from the viewpoint of efficiently extracting the chlorogenic acid from the sunflower seed residues remaining after oil expression, the extraction solvent is preferably an alcohol or a liquid mixture of water and an alcohol. From the viewpoint of efficiently decomposing the saccharides by alcohol fermentation caused by yeast, the extraction solvent is preferably water or a liquid mixture of water and an alcohol, and more preferably water.

Examples of the alcohol include ethanol, methanol, isopropyl alcohol, and the like. Two or more kinds of alcohols may be used by being mixed together. In a case where the finally obtained chlorogenic acid is used in a drink or food item (for example, a health food, a food additive, or the like), from the viewpoint of safety, the alcohol is preferably ethanol.

In a case where the liquid mixture of water and an alcohol is used as the extraction solvent, the mass ratio of water to the alcohol (water/alcohol) is preferably 1/1,000 to 1,000/1. From the viewpoint of the extraction efficiency of the chlorogenic acid and the efficiency of saccharide decomposition caused by yeast, the mass ratio of water/alcohol is more preferably 1/1 to 100/1.

Examples of preferred embodiments of the chlorogenic acid extraction step in the present invention include the following 3 embodiments.

1. A first embodiment in which the chlorogenic acid extraction step is constituted with a step (hereinafter, referred to as "Step I-I") of obtaining a liquid extract by bringing sunflower seed residues remaining after oil expression into contact with the aforementioned solvent and a step (hereinafter, referred to as "Step I-II") of obtaining a chlorogenic acid-containing liquid extract by bringing the obtained liquid extract into contact with yeast.

2. A second embodiment in which the chlorogenic acid extraction step is constituted with a step (hereinafter, referred to as "Step II-I") of obtaining a mixture by mixing sunflower seed residues remaining after oil expression with yeast and a step (hereinafter, referred to as "Step II-II") of obtaining a chlorogenic acid-containing liquid extract by bringing the obtained mixture into contact with the aforementioned solvent.

3. A third embodiment in which the chlorogenic acid extraction step is constituted with a step (hereinafter, referred to as "Step III") of obtaining a chlorogenic acid-containing liquid extract by bringing sunflower seed residues remaining after oil expression into contact with the aforementioned solvent in the presence of yeast.

Hereinafter, these 3 embodiments will be described.

<First Embodiment>

The first embodiment of the chlorogenic acid extraction step in the present invention includes a step (hereinafter, referred to as "Step I-I") of obtaining a liquid extract by bringing sunflower seed residues remaining after oil expression into contact with the aforementioned solvent and a step (hereinafter, referred to as "Step I-II") of obtaining a chlorogenic acid-containing liquid extract by bringing the obtained liquid extract into contact with yeast.

(Step I-I)

In Step I-I, a liquid extract containing chlorogenic acid and saccharides can be obtained from sunflower seed residues remaining after oil expression.

In Step I-I, the method for obtaining the liquid extract by bringing the sunflower seed residues remaining after oil expression into contact with the aforementioned solvent is not particularly limited. However, examples of the method include a method for obtaining a liquid extract by adding the sunflower seed residues remaining after oil expression to the solvent, heating and stirring the resultant, and then removing the extraction residues of the sunflower seed residues remaining after oil expression by performing solid-liquid separation, a method for obtaining a liquid extract by passing the solvent through a column filled with the sunflower seed residues remaining after oil expression at normal temperature or a high temperature under normal pressure conditions or pressurized conditions, and the like.

The solid-liquid separation method is not particularly limited, and examples thereof include methods such as filtration (for example, suction filtration, pressure filtration, or the like), centrifugation, and compression.

During the solid-liquid separation by filtration, a filter aid may be used. Examples of the filter aid include diatomite, pearlite, cellulose, and products obtained by processing these.

During the solid-liquid separation in Step I-I, from the viewpoint of increasing the amount of chlorogenic acid obtained, it is desirable to wash the extraction residues of the removed sunflower seed residues remaining after oil expression with a new solvent after the first solid-liquid separation and then to recover the obtained washing solution as a liquid extract.

In Step I-I, the amount of the solvent brought into contact with the sunflower seed residues remaining after oil expression is preferably 3 times to 50 times and more preferably 5 times to 20 times greater than the amount of the sunflower seed residues remaining after oil expression in terms of a mass ratio.

In Step I-I, the temperature at the time of bringing the sunflower seed residues remaining after oil expression into contact with the solvent, which is a so-called extraction temperature, is appropriately selected according to the type of the solvent. For example, in a case where the solvent is water, from the viewpoint of the extraction efficiency, the extraction temperature is preferably 10° C. to 100° C., and more preferably 30° C. to 100° C. For example, in a case where the solvent is an alcohol, from the viewpoint of the extraction efficiency, the extraction temperature is preferably 10° C. to 90° C., and more preferably 30° C. to 90° C. For example, in a case where the solvent is a liquid mixture of water and an alcohol (mass ratio: water/alcohol=50/50), from the viewpoint of the extraction efficiency, the extraction temperature is preferably 10° C. to 100° C., and more preferably 30° C. to 100° C.

In Step I-I, the time for which the sunflower seed residues remaining after oil expression are brought into contact with the solvent, which is a so-called extraction time, is appropriately selected according to the type of the solvent, the extraction temperature, and the like. Generally, the extraction time is 1 hour to 24 hours.

(Step I-II)

In Step I-II, by bringing the liquid extract obtained in Step I-I that contains chlorogenic acid and saccharides into contact with yeast, the saccharides (for example, sucrose, raffinose, or the like) contained in the liquid extract are decomposed into carbon dioxide, ethanol, and the like by alcohol fermentation caused by yeast. In this way, the calories resulting from the saccharides contained in the liquid extract can be reduced. In contrast, because the chlorogenic acid is not decomposed by the yeast, it is possible to obtain a chlorogenic acid-containing liquid extract in which the calories resulting from lipid are reduced.

In a case where the solvent in Step I-I is not water, from the viewpoint of efficiently decomposing the saccharides by alcohol fermentation caused by yeast in Step I-II, the solvent of the liquid extract obtained in Step I-I that contains the chlorogenic acid and saccharides may be substituted with water in Step I-II such that the liquid extract becomes in the form of water containing the chlorogenic acid and saccharides, and then the liquid extract may be brought into contact with yeast.

In Step I-II, the method for obtaining the chlorogenic acid-containing liquid extract by bringing the liquid extract obtained in Step I-I that contains the chlorogenic acid and saccharides into contact with yeast is not particularly limited. Examples of the method include a method for obtaining a chlorogenic acid-containing liquid extract by adding yeast to the liquid extract obtained in Step I-I that contains the chlorogenic acid and saccharides, stirring the resultant, and then removing the yeast fungi by performing solid-liquid separation.

The solid-liquid separation method is not particularly limited, and examples thereof include methods such as filtration (for example, suction filtration, pressure filtration, and the like), centrifugation, and compression.

During the solid-liquid separation by filtration, a filter aid may be used. As the filter aid, it is possible to use the same ones as used in Step I-I described above.

In the solid-liquid separation in Step I-II, from the viewpoint of increasing the amount of the chlorogenic acid obtained, it is desirable to wash the removed yeast fungi with a new solvent after the first solid-liquid separation and to recover the obtained washing solution as a chlorogenic acid-containing liquid extract.

In Step I-II, the amount of the yeast brought into contact with the liquid extract obtained in Step I-I that contains the chlorogenic acid and saccharides is not particularly limited as long as the amount is enough for decomposing the saccharides contained in the liquid extract, and an excess of yeast may be used. Generally, the amount of the yeast in Step I-II is preferably 1/1,000 to 1/1 and more preferably 1/100 to 1/10 in terms of a mass ratio, with respect to the sunflower seed residues remaining after oil expression in Step I-I.

In Step I-II, from the viewpoint of efficiently decomposing the saccharides by alcohol fermentation caused by the yeast, the temperature at the time of bringing the liquid extract obtained in Step I-I that contains the chlorogenic acid and saccharides into contact with the yeast is preferably 20° C. to 50° C., and more preferably 30° C. to 40° C.

The chlorogenic acid-containing liquid extract obtained through Step I-I and Step I-II as described above is subjected to the next step, a bacterial treatment step.

<Second Embodiment>

The second embodiment of the chlorogenic acid extraction step in the present invention includes a step (hereinafter, referred to as "Step II-I") of obtaining a mixture by mixing sunflower seed residues remaining after oil expression with yeast and a step (hereinafter, referred to as "Step II-II") of obtaining a chlorogenic acid-containing liquid extract by bringing the obtained mixture into contact with the aforementioned solvent.

(Step II-I)

In Step II-I, in a case where the sunflower seed residues remaining after oil expression contain moisture, whether the yeast is live yeast or dry yeast, the saccharides (for example, sucrose, raffinose, or the like) contained in the sunflower seed residues remaining after oil expression can be decomposed by alcohol fermentation caused by the yeast. In this case, from the viewpoint of efficiently decomposing the saccharides by the alcohol fermentation caused by the yeast, the temperature at the time of mixing the sunflower seed residues remaining after oil expression with the yeast is preferably 20° C. to 50° C., and more preferably 30° C. to 40° C.

In Step II-I, the amount of the yeast mixed with the sunflower seed residues remaining after oil expression is not particularly limited as long as the amount is enough for decomposing the saccharides contained in the sunflower seed residues remaining after oil expression, and an excess of yeast may be used. Generally, the amount of the yeast in Step II-I is preferably 1/1,000 to 1/1 and more preferably 1/100 to 1/10 in terms of a mass ratio, with respect to the sunflower seed residues remaining after oil expression.

(Step II-II)

In Step II-II, a chlorogenic acid-containing liquid extract can be obtained from the sunflower seed residues remaining after oil expression. In a case where the yeast in Step II-I is dry yeast and the sunflower seed residues remaining after oil expression do not contain moisture, for example, in a case where the yeast cannot decompose the saccharides contained in the sunflower seed residues remaining after oil expression, the extraction of chlorogenic acid from the sunflower seed residues remaining after oil expression and the yeast-mediated decomposition of the saccharides contained in the sunflower seed residues remaining after oil expression are performed at the same time in Step II-II.

In Step II-II, the method for obtaining a chlorogenic acid-containing liquid extract by bringing the mixture obtained in Step II-I into contact with the aforementioned solvent is not particularly limited. Examples of the method include a method for obtaining a chlorogenic acid-containing liquid extract by adding the mixture obtained in Step II-I to a solvent, heating and stirring the resultant, and then removing the extraction residues of the sunflower seed residues remaining after oil expression and the yeast fungi by performing solid-liquid separation, a method for obtaining a chlorogenic acid-containing liquid extract by passing a solvent through a column filled with the mixture obtained in Step II-I at normal temperature or a high temperature under normal pressure conditions or pressurized conditions, and the like.

The solid-liquid separation method is not particularly limited, and examples thereof include methods such as filtration (for example, suction filtration, pressure filtration, and the like), centrifugation, and compression.

During the solid-liquid separation by filtration, a filter aid may be used. As the filter aid, it is possible to the same filter aid as used in Step I-I in the first embodiment described above.

During the solid-liquid separation in Step II-II, from the viewpoint of increasing the amount of chlorogenic acid obtained, it is desirable to wash the extraction residues of the removed sunflower seed residues remaining after oil expression and the removed yeast fungi with a new solvent after the first solid-liquid separation and to recover the obtained washing solution as a chlorogenic acid-containing liquid extract.

In Step II-II, the amount of the solvent brought into contact with the mixture obtained in Step II-I is preferably 3 times to 50 times and more preferably 5 times to 20 times greater than the amount of the mixture obtained in Step II-I in terms of a mass ratio.

The temperature at the time of bringing the mixture obtained in Step II-I into contact with the solvent in Step II-II, which is a so-called extraction temperature, is the same as the extraction temperature in Step I-I described above. In a case where the saccharides contained in the sunflower seed residues remaining after oil expression are decomposed by yeast in Step II-II, from the viewpoint of efficiently decomposing the saccharides by alcohol fermentation caused by yeast, the extraction temperature is preferably 20° C. to 50° C., and more preferably 30° C. to 40° C.

In Step II-II, the time for which the mixture obtained in Step II-I is brought into contact with the solvent, which is a so-called extraction time, is the same as the extraction time in Step I-I in the first embodiment described above.

The chlorogenic acid-containing liquid extract obtained through Step II-I and Step II-II as described above is subjected to the next step, a bacterial treatment step.

<Third Embodiment>

The third embodiment of the chlorogenic acid extraction step in the present invention includes a step (hereinafter, referred to as "Step III") of obtaining a chlorogenic acid-containing liquid extract by bringing sunflower seed residues remaining after oil expression into contact with the aforementioned solvent in the presence of yeast.

(Step III)

According to Step III, the extraction of chlorogenic acid and the yeast-mediated decomposition of the saccharides contained in the sunflower seed residues remaining after oil expression can be performed at the same time.

The method for obtaining a chlorogenic acid-containing liquid extract by bringing the sunflower seed residues remaining after oil expression into contact with the aforementoined solvent in the presence of yeast is not particularly limited. Examples of the method include a method for obtaining a chlorogenic acid-containing liquid extract in which an operation of adding sunflower seed residues remaining after oil expression and yeast to a solvent and heating and stirring the resultant or an operation of adding sunflower seed residues remaining after oil expression to a solvent, heating and stirring the resultant, then adding yeast thereto, and heating and stirring the resultant is performed, and then the extraction residues of the sunflower seed residues remaining after oil expression and the yeast fungi are removed by performing solid-liquid separation, and the like.

The solid-liquid separation method is not particularly limited, and the methods known in the related art can be adopted. Examples thereof include methods such as filtration (for example, suction filtration, pressure filtration, and the like), centrifugation, and compression.

The amount of the yeast in Step III is not particularly limited as long as the amount is enough for decomposing the saccharides contained in the sunflower seed residues remaining after oil expression, and an excess of yeast may be used. Generally, the amount of the yeast in Step III is preferably 1/1,000 to 1/1 and more preferably 1/100 to 1/10 with respect to the sunflower seed residues remaining after oil expression in terms of a mass ratio.

In Step III, the temperature at the time of bringing the sunflower seed residues remaining after oil expression into contact with the solvent, which is a so-called extraction temperature, is the same as the extraction temperature in Step I-I in the first embodiment described above. From the viewpoint of efficiently decomposing the saccharides by alcohol fermentation caused by yeast, the extraction temperature is preferably 20° C. to 50° C., and more preferably 30° C. to 40° C.

In Step III, the time for which the sunflower seed residues remaining after oil expression are brought into contact with a solvent, which is a so-called extraction time, is the same as the extraction time in Step I-I in the first embodiment described above.

The chlorogenic acid-containing liquid extract obtained through Step III as described above is subjected to the next step, a bacterial treatment step.

<Bacterial Treatment Step>

The method for manufacturing a chlorogenic acid-containing composition of the present invention includes a bacterial treatment step of performing at least one treatment selected from germicidal treatment or sterilization treatment on the chlorogenic acid-containing liquid extract obtained by the chlorogenic acid extraction step.

If viable cells of yeast or other bacteria (for example, spoilage bacteria contained in the sunflower seed residues remaining after oil expression, airborne bacteria, and the like) remain in the chlorogenic acid-containing liquid extract, the chlorogenic acid may be decomposed or altered, and this may lead to deterioration of stability of the chlorogenic acid-containing composition. According to the bacterial treatment step in the present invention, the yeast and other bacteria are killed or removed, and hence the finally obtained chlorogenic acid-containing composition is excellent in the quality stability and the preservation stability.

The method of the germicidal treatment or sterilization treatment in the bacterial treatment step is not particularly limited, and methods known in the related art can be used.

Examples of the germicidal treatment include heating treatment, ultraviolet treatment, electromagnetic wave treatment, high-pressure treatment, ozone treatment, germicide treatment, alcohol treatment, and the like. Among these, heating treatment is preferable as the germicidal treatment. The heating temperature is preferably equal to or higher than 60° C., more preferably equal to or higher than 70° C., and even more preferably equal to or higher than 80° C. The upper limit of the heating temperature is not particularly limited but is generally equal to or lower than 250° C. The heating time is not particularly limited. However, it is generally equal to or longer than 1 second and preferably equal to or longer than 10 minutes.

Examples of the sterilization treatment include sterilization treatments using, for example, a membrane filter, an ultrafiltration (UF) membrane, a nanofiltration (NF) membrane, a reverse osmosis (RO) membrane, and the like. Among these, sterilization treatment using a membrane filter and sterilization treatment using an ultrafiltration membrane are preferable as the sterilization treatment. The diameter of pores of the membrane filter is preferably equal to or less than 0.5 μm and more preferably equal to or less than 0.3 μm.

One kind of the germicidal treatment and the sterilization treatment may be performed singly, or two or more kinds thereof may be performed in combination.

<Other Steps>

If necessary, the method for manufacturing a chlorogenic acid-containing composition of the present invention may include, in addition to the chlorogenic acid extraction step and the bacterial treatment step described above, other steps within a scope that does not impair the effects of the present invention.

Examples of other steps include a step of obtaining chlorogenic acid-containing composition powder by drying the chlorogenic acid-containing liquid extract after the bacterial treatment step described above. Herein, the chlorogenic acid-containing liquid extract may be dried after being concentrated.

Examples of the method for concentrating the chlorogenic acid-containing liquid extract include methods such as vacuum concentration, and thin-film concentration.

Examples of the method for obtaining the chlorogenic acid-containing composition powder by drying the chlorogenic acid-containing liquid extract or a concentrate thereof include a spray drying method, a freeze-drying method, a thin-film drying method, and the like.

The chlorogenic acid-containing liquid extract or the concentrate thereof that has not yet been dried may be subjected to purification treatment using an ultrafiltration membrane.

According to the purpose of usage, the chlorogenic acid-containing composition powder may be further subjected to post-treatment such as recrystallization or purification treatment using column chromatography.

[Chlorogenic Acid-Containing Composition]

In the method for manufacturing a chlorogenic acid-containing composition of the present invention, sunflower seed residues remaining after oil expression are used as a raw material. Therefore, unlike a case where sunflower seeds are used, a chlorogenic acid-containing composition in which the calories resulting from lipid are reduced is obtained.

Furthermore, in the method for manufacturing a chlorogenic acid-containing composition of the present invention, the saccharides such as sucrose and raffinose contained in the sunflower seed residues remaining after oil expression are decomposed by alcohol fermentation caused by yeast. Therefore, a chlorogenic acid-containing composition in which calories resulting from the saccharides are reduced is obtained.

Accordingly, the chlorogenic acid-containing composition obtained by the manufacturing method of the present invention reduces the concerns about hyperglycemia, obesity, and the like that may be caused by the intake of the composition. Consequently, the chlorogenic acid-containing composition is suitable for being used in, for example, foods including drinks (hereinafter, referred to as a drink or food item) or pharmaceutical products. Examples of the drink or food item include health foods, food additives, and the like.

In addition, in the method for manufacturing a chlorogenic acid-containing composition of the present invention, at least one treatment selected from germicidal treatment or sterilization treatment is performed on the chlorogenic acid-containing liquid extract. Therefore, there are no concerns about decomposition, alteration, and the like of the chlorogenic acid caused by yeast or other bacteria.

Accordingly, the chlorogenic acid-containing composition obtained by the manufacturing method of the present invention is excellent in quality stability and preservation stability. Consequently, the chlorogenic acid-containing composition can be suitably used as an active component of, for example, a drink or food item, a pharmaceutical product, or cosmetics, directly or after being appropriately treated.

Moreover, the method for manufacturing a chlorogenic acid-containing composition of the present invention does not include a step in which a chemical reaction that may change the structure of the chlorogenic acid is performed. Therefore, there is no concern about the generation of a byproduct.

Accordingly, the chlorogenic acid-containing composition obtained by the manufacturing method of the present invention is highly safe and is suitable for being used particularly in a drink or food item, a pharmaceutical product, or cosmetics.

In a case where the chlorogenic acid-containing composition of the present invention is used in a drink or food item, a pharmaceutical product, or cosmetics, according to the purpose, various components other than the components originally contained in the chlorogenic acid-containing composition of the present invention can be added thereto.

Examples of other components include saccharides (sorbitol, D-sorbitol, glucitol, mannitol, glucose, sucrose, lactose, maltose, maltitol, trehalose, and the like), animal and vegetable extracts, amino acids, vitamins, *lactobacillus* (living cells or dead cells), and the like.

In a case where the chlorogenic acid-containing composition of the present invention is used in a drink or food item, examples of components that can be concurrently used include a sweetener, an acidulant, a flavor modifier such as an amino acid-containing seasoning, fragrance, a germicide, a preservative, an antioxidant, a surfactant, and the like that are different from and do not correspond to other components described above.

In a case where the chlorogenic acid-containing composition of the present invention is used in cosmetics or skin care preparations for external use, general-purpose oil and fat which can become a base of cosmetics or pharmaceutical preparations, waxes, hydrocarbon oils, fatty acids, alcohols, esters, silicones, powder, and the like may be concurrently used. In addition, in a case where the chlorogenic acid-containing composition of the present invention is used in cosmetics or skin care preparations for external use, examples of the components that can be concurrently used include an oleaginous component, a moisturizer, an ultraviolet absorber, a germicide, a preservative, an antioxidant, a sequestrant, fragrance, a colorant, an extender pigment, and the like.

In a case where the chlorogenic acid-containing composition of the present invention is used in a drink or food item, a pharmaceutical product, or cosmetics, the amount of chlorogenic acids contained in the products of the drink or food item, pharmaceutical product, or cosmetics is not particularly limited and may be appropriately adjusted according to the purpose. For example, the content of chlorogenic acids in the products of the drink or food item, pharmaceutical product, or cosmetics is preferably equal to or greater than 0.0001% and equal to or less than 30% with respect to the products in terms of a mass ratio. Particularly, in a case where the chlorogenic acid-containing composition of the present invention is used in a drink or food item, the content of chlorogenic acid in the product of the drink or food item is preferably equal to or greater than 0.001% and equal to or less than 20% with respect to the products in terms of a mass ratio.

EXAMPLES

Hereinafter, the present invention will be more specifically described based on examples. However, as long as the scope of the present invention is maintained, the present invention is not limited to the following examples.

Comparative Example 1

50 g of sunflower seed residues remaining after oil expression were added to 350 mL of water, and the resultant was stirred for 5 hours at 40° C. in a nitrogen atmosphere. The obtained stirred substance was cooled to room temperature and then subjected to suction filtration using Nutsche coated with 15 g of celite, thereby obtaining residues and a first liquid extract. Furthermore, the obtained residues were washed with 100 mL of water, thereby obtaining a second liquid extract.

The obtained first liquid extract and second liquid extract were subjected to vacuum concentration and then to freeze drying, thereby obtaining 8.60 g of powder.

The obtained powder was subjected to $^1$H-NMR analysis. As a result, it was confirmed that one of the components thereof was chlorogenic acid.

The content of chlorogenic acids in the obtained powder was analyzed by HPLC. As a result, it was confirmed that the total content of the chlorogenic acids was 955 mg.

Furthermore, the content of each of sucrose, raffinose, melibiose in the obtained powder was analyzed by HPLC. As a result, it was confirmed that the content of sucrose was 1.80 g and the content of raffinose was 1.26 g. Melibiose was not detected (detection limit: 0.2 mg).

Example 1

50 g of sunflower seeds residues remaining after oil expression and 2.5 g of dry baker's yeast (manufactured by Oriental Yeast Co., ltd.) were added to 350 mL of water, and the resultant was stirred for 5 hours at 40° C. in a nitrogen atmosphere. The obtained stirred substance was cooled to room temperature and then subjected to suction filtration using Nutsche coated with 15 g of celite, thereby obtaining residues and a first liquid extract. Furthermore, the obtained residues were washed with 100 mL of water, thereby obtaining a second liquid extract.

The obtained first liquid extract and second liquid extract were subjected to germicidal treatment by being heated for 30 minutes at 85° C. to 90° C. The liquid extracts having undergone the germicidal treatment were subjected to vacuum concentration and then to freeze drying, thereby obtaining 6.92 g of powder.

The obtained powder was subjected to $^1$H-NMR analysis. As a result, similarly to Comparative example 1, it was confirmed that one of the components thereof was chlorogenic acid.

The content of chlorogenic acids in the obtained powder was analyzed by high performance liquid chromatography (HPLC). As a result, it was confirmed that the total content of the chlorogenic acids was 955 mg.

Furthermore, the content of each of sucrose, raffinose, and melibiose in the obtained powder was analyzed by HPLC. As a result, it was confirmed that the content of both the sucrose and raffinose was equal to or less than the detection limit (sucrose: 0.2 mg, raffinose: 0.2 mg). In contrast, it was confirmed that the content of melibiose was 680 mg.

The calories (energy) of the powder obtained in Example 1 and the calories of the powder obtained in Comparative example 1 were calculated respectively using an energy conversion coefficient of Atwater (sucrose: 4 kcal/g, raffinose: 2 kcal/g, melibiose: 2 kcal/g), and the calories of the powders were compared to each other. As a result, it was confirmed that the calories of the powder obtained in Example 1 were lower than the calories of the powder obtained in Comparative example 1, by 8.76 kcal per 1 g of chlorogenic acid.

Example 2

50 g of sunflower seed residues remaining after oil expression were added to 350 mL of water, and the resultant was stirred for 5 hours at 40° C. in a nitrogen atmosphere. The obtained stirred substance was cooled to room temperature and then subjected to suction filtration using Nutsche coated with 15 g of celite, thereby obtaining residues and a first liquid extract. Furthermore, the obtained residues were washed with 100 mL of water, thereby obtaining a second liquid extract.

2.5 g of dry baker's yeast (manufactured by Oriental Yeast Co., ltd.) was added to the obtained first liquid extract and second liquid extract, and the resultant was stirred for 5 hours at 40° C. in a nitrogen atmosphere. The obtained stirred substance was cooled to room temperature and then subjected to suction filtration using Nutsche coated with 15 g of celite, thereby obtaining solid contents and a first filtrate. Furthermore, the obtained solid contents were washed with 100 mL of water, thereby obtaining a second filtrate.

The obtained first filtrate and second filtrate were passed through an ultrafiltration membrane (manufactured by Merck Millipore Corporation., Amicon Ultra-15, molecular weight cutoff: 10 kDa) and then subjected to vacuum concentration, followed by freeze drying, thereby obtaining 4.93 g of powder.

The obtained powder was subjected to $^1$H-NMR analysis. As a result, similarly to Comparative example 1, it was confirmed that one of the components thereof was chlorogenic acid.

The content of chlorogenic acids in the obtained powder was analyzed by HPLC. As a result, it was confirmed that the total content of the chlorogenic acids was 950 mg.

Furthermore, the content of each of sucrose, raffinose, and melibiose in the obtained powder was analyzed by HPLC. As a result, it was confirmed that the content of both the sucrose and raffinose was equal to or less than the detection limit (sucrose: 0.2 mg, raffinose: 0.2 mg). In contrast, it was confirmed that the content of melibiose was 750 mg.

The calories (energy) of the powder obtained in Example 2 were calculated using an energy conversion coefficient of Atwater (sucrose: 4 kcal/g, raffinose: 2 kcal/g, melibiose: 2 kcal/g), and compared with the calories of the powder obtained in Comparative example 1 calculated as above. As a result, it was confirmed that the calories of the powder obtained in Example 2 were lower than the calories of the powder obtained in Comparative example 1, by 8.60 kcal per 1 g of chlorogenic acid.

The above results clearly showed that while the content of chlorogenic acid in the powders (hereinafter, referred to as "powder of Example 1" and "powder of Example 2" respectively) obtained by the manufacturing method of Examples 1 and 2 in which solvent extraction is performed using yeast is equivalent to the content of chlorogenic acid in the powder (hereinafter, referred to as "powder of Comparative example 1") obtained by the manufacturing method of Comparative example 1 in which only the solvent extraction is performed without using yeast, the calories per 1 g of chlorogenic acid are lower in the powder of Example 1 and the powder of Example 2 using yeast than in the powder of Comparative example 1.

Sucrose and raffinose confirmed in the powder of Comparative example 1 were not detected from the powder of Example 1 and the powder of Example 2. Furthermore, melibiose not confirmed in the powder of Comparative example 1 was confirmed in the powder of Example 1 and the powder of Example 2. Therefore, it is considered that the calories are reduced due to the yeast-mediated decomposition of saccharides such as sucrose and raffinose.

[Quantification of Chlorogenic Acid]

The chlorogenic acid in the powder was quantified by an absolute calibration curve method by reverse-phase HPLC including a UV detector. The calibration curve was created using standard chlorogenic acid (manufactured by Wako Pure Chemical Industries, Ltd.) under the same HPLC conditions as used at the time of quantification.

[Quantification of Sucrose, Raffinose, and Melibiose]

Sucrose, raffinose, and melibiose in the powder were quantified by an absolute calibration curve method by normal-phase HPLC including an RI detector. The calibration curves were created using standard sucrose, standard raffinose, and standard melibiose (all manufactured by Wako Pure Chemical Industries, Ltd.) under the same HPLC conditions as used at the time of quantification.

Example 3

[Preparation of Chlorogenic Acid-Containing Drink]

300 mg of powder (chlorogenic acid-containing composition) obtained in Example 1 was dissolved in 500 ml of water, thereby preparing a drink (chlorogenic acid-containing drink) containing the chlorogenic acid-containing composition. The chlorogenic acid-containing drink was subjected to a sensory test. As a result, it was confirmed that both the taste and scent of the drink were preferable.

The entire disclosures of JP2013-209537 filed on Oct. 4, 2013 and JP2014-023856 filed on Feb. 10, 2014 are incorporated into the present specification by reference.

All of the documents, patent applications, and technical specifications described in the present specification are incorporated into the present specification by reference, as if the documents, patent applications, and technical specifications are specifically and individually incorporated into the present specification by reference.

What is claimed is:

1. A method for manufacturing a chlorogenic acid-containing composition, comprising:
    expressing oil from sunflower seeds to obtain a residue, wherein said residue comprises chlorogenic acid and saccharides;
    contacting said residue with an effective amount of yeast and an extraction solvent selected from the group consisting of water, an alcohol, and a mixture of water and an alcohol at an extraction temperature of 10° C. to 100° C. for 1 hour to 24 hours to obtain a chlorogenic acid-containing liquid extract;
    performing at least one treatment selected from a germicidal treatment or a sterilization treatment on the liquid extract to obtain said chlorogenic acid-containing composition.

2. The method for manufacturing a chlorogenic acid-containing composition according to claim 1, wherein an amount of the solvent is 3 times to 50 times the amount of the residue in terms of a mass ratio, and the amount of the yeast is 1/1,000 to 1/1 of the amount of the residue in terms of a mass ratio.

3. The method for manufacturing a chlorogenic acid-containing composition according to claim 1, wherein contacting the liquid extract and the yeast is performed at a temperature of 20° C. to 50° C.

4. The method for manufacturing a chlorogenic acid-containing composition according to claim 1, wherein the contacting said residue includes mixing the residue with the yeast to obtain a mixture, and bringing the obtained mixture into contact with the extraction solvent.

5. The method for manufacturing a chlorogenic acid-containing composition according to claim 4, wherein an amount of the solvent is 3 times to 50 times the amount of the residue in terms of a mass ratio, and the amount of the yeast is 1/1,000 to 1/1 of the amount of the residue in terms of a mass ratio.

6. The method for manufacturing a chlorogenic acid-containing composition according to claim 4, wherein the mixing of the residues with the yeast is performed at a temperature of 20° C. to 50° C.

7. The method for manufacturing a chlorogenic acid-containing composition according to claim 1, wherein the yeast is baker's yeast.

8. The method for manufacturing a chlorogenic acid-containing composition according to claim 1, wherein the solvent is water.

9. The method for manufacturing a chlorogenic acid-containing composition according to claim 1, further comprising: drying the chlorogenic-acid containing composition to form a powder.

* * * * *